United States Patent
Flieg et al.

(10) Patent No.: US 11,517,855 B2
(45) Date of Patent: Dec. 6, 2022

(54) LIVER SUPPORT SYSTEM DEVICES AND METHODS THEREOF

(71) Applicant: GAMBRO LUNDIA AB, Lund (SE)

(72) Inventors: Ralf Flieg, Rangendingen (DE); Bernd Krause, Rangendingen (DE); Markus Storr, Filderstadt (DE)

(73) Assignee: GAMBRO LUNDIA AB, Lund (SE)

( * ) Notice: Subject to any disclaimer, the term of this patent is extended or adjusted under 35 U.S.C. 154(b) by 758 days.

(21) Appl. No.: 16/328,478

(22) PCT Filed: Sep. 5, 2017

(86) PCT No.: PCT/EP2017/072154
§ 371 (c)(1),
(2) Date: Feb. 26, 2019

(87) PCT Pub. No.: WO2018/046461
PCT Pub. Date: Mar. 15, 2018

(65) Prior Publication Data
US 2019/0193028 A1 Jun. 27, 2019

(30) Foreign Application Priority Data
Sep. 6, 2016 (EP) .................................. 16187466

(51) Int. Cl.
*B01D 61/24* (2006.01)
*A61M 1/16* (2006.01)
(Continued)

(52) U.S. Cl.
CPC ......... *B01D 61/243* (2013.01); *A61M 1/1633* (2014.02); *A61M 1/1676* (2014.02);
(Continued)

(58) Field of Classification Search
None
See application file for complete search history.

(56) References Cited

U.S. PATENT DOCUMENTS

| | | | |
|---|---|---|---|
| 5,891,338 A | 4/1999 | Bell | |
| 2015/0273127 A1* | 10/2015 | Flieg | A61M 1/3472 210/266 |
| 2015/0290380 A1* | 10/2015 | Welzel | A61M 1/3472 210/638 |

FOREIGN PATENT DOCUMENTS

| EP | 0 615 780 A1 | 9/1994 |
|---|---|---|
| EP | 2 113 298 A1 | 11/2009 |
| | (Continued) | |

OTHER PUBLICATIONS

Stauber et al., Transplantationsmedizin, 2010; 22:333-338.
(Continued)

*Primary Examiner* — Hayden Brewster
(74) *Attorney, Agent, or Firm* — Barnes & Thornburg LLP (57) ABSTRACT

The present disclosure relates to an artificial, extracorporeal system for supporting the function of the liver of a patient suffering from liver failure, which is characterized in that it comprises a first high-flux or high cut-off hollow fiber membrane dialyzer which is perfused on the lumen side with the patient's blood and wherein a buffered aqueous solution comprising human serum albumin is passed in a continuous flow through the filtrate space of said first dialyzer, a second hollow fiber membrane dialyzer which removes water-soluble substances from the dialysate of said first dialyzer, and a third, integrated hollow fiber membrane dialyzer which is perfused with the retentate of second hemodialyzer and which allows the passage of certain amounts of albumin over the membrane wall into the filtrate space which is populated with adsorbent material. The system can be used for the treatment of acute liver failure and acute-on-chronic liver failure.

20 Claims, 4 Drawing Sheets

(51) Int. Cl.
*B01D 61/28* (2006.01)
*B01D 69/02* (2006.01)

(52) U.S. Cl.
CPC .......... *A61M 1/1696* (2013.01); *B01D 61/28* (2013.01); *B01D 69/02* (2013.01); *B01D 2311/06* (2013.01); *B01D 2311/2626* (2013.01); *B01D 2317/025* (2013.01); *B01D 2325/20* (2013.01)

(56) References Cited

FOREIGN PATENT DOCUMENTS

| | | |
|---|---|---|
| EP | 2380610 | 10/2011 |
| EP | 2735359 | 5/2014 |
| EP | 2735326 | 5/2015 |
| WO | WO 2004/056460 | 7/2004 |
| WO | WO 2011/131534 | 10/2011 |
| WO | WO 2014/079680 | 5/2014 |
| WO | WO 2014/079681 | 5/2014 |

OTHER PUBLICATIONS

Boldt, Br. J. Anaesth., 2010; 104 (3):276-284.
PCT Search Report and Written Opinion prepared for PCT/EP2017/072154, completed Sep. 20, 2017.
Boschetti-De-Fierro, Adriana, et al., "Extended characterization of a new class of membranes for blood purification: The high cut-off membranes," Jul. 1, 2013; International Journal of Artificial Organs; vol. 36, Nr: 7, pp. 455-463.

* cited by examiner

LIVER SUPPORT SYSTEM DEVICES AND METHODS THEREOF

CROSS-REFERENCE TO RELATED APPLICATIONS

This application is the U.S. national phase of PCT/EP2017/072154, filed on Sep. 5, 2017, which claims the benefit of European Patent Application Serial Number 16187466.4, filed on Sep. 6, 2016, the entire disclosures of both of which are incorporated herein by reference.

TECHNICAL FIELD

Figure 1:
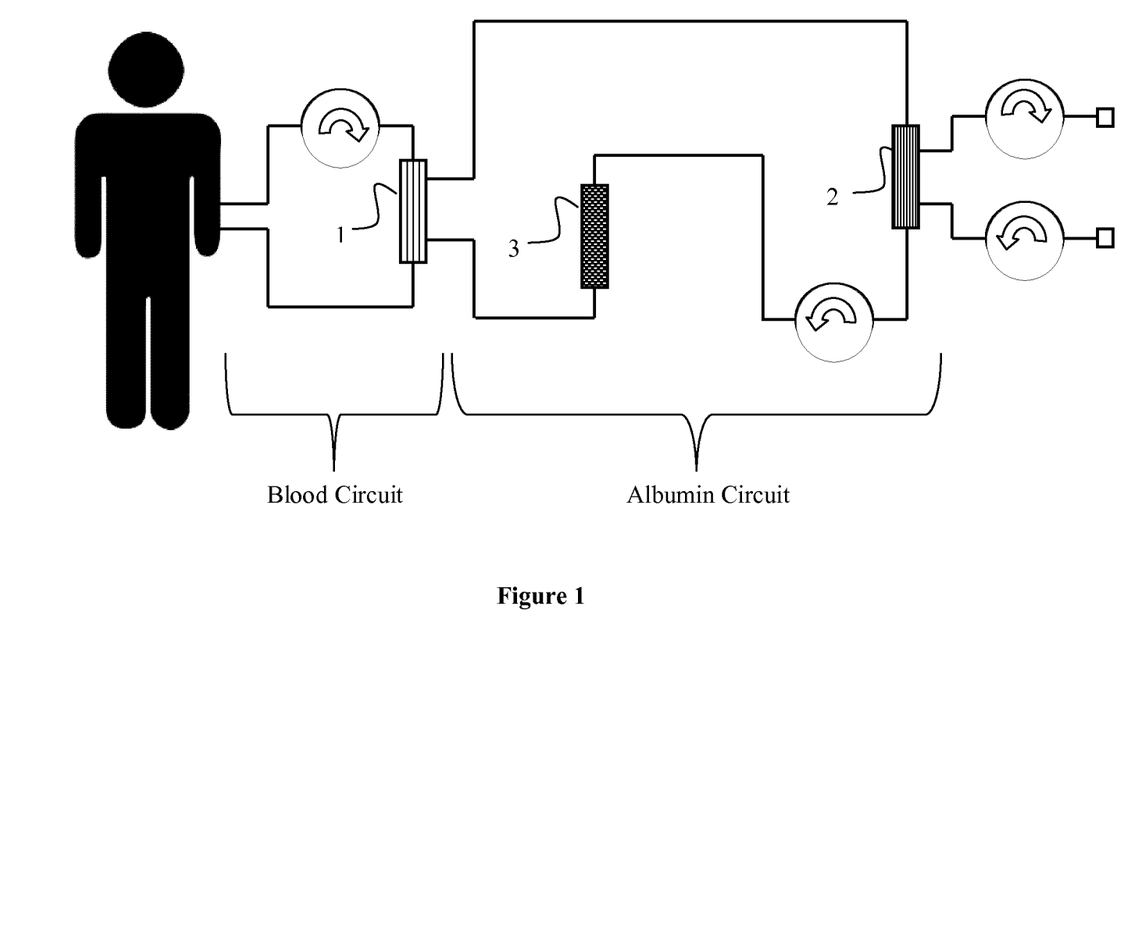

The present disclosure relates to an artificial, extracorporeal system for liver replacement and/or assistance, comprising a liver dialysis device for conducting hemodialysis on a patient suffering from liver failure, which is characterized in that it comprises a first standard hollow fiber membrane dialyzer which is perfused with the patient's blood, a second hollow fiber membrane dialyzer which removes water-soluble substances from the dialysate of said first dialyzer, and a third, integrated hollow fiber membrane dialyzer which allows the passage of certain amounts of albumin over the membrane wall and which is perfused with the dialysate which leaves said second hemodialyzer (FIG. 1). The filtrate space of the third, integrated hollow fiber membrane dialyzer is in fluid connection only with the lumen space of the hollow fibers and is populated with a chemically and/or physically active adsorbent material which may comprise one or more different substances, such as hydrophobic adsorbents and/or ion exchange material. The system can be used for the treatment of acute liver failure and acute-on-chronic liver failure.

DESCRIPTION OF THE RELATED ART

There is a need to develop or improve artificial systems and devices for liver replacement and/or assistance which are used to either support patients with borderline function of their liver until their liver regenerates or until a donor liver is obtained for transplantation. Several systems are known in the prior art today which serve this purpose. In principle, such liver support, often also referred to as liver dialysis, is a detoxification treatment and is used for patients with various liver disorders, such as, for example, hepatorenal syndrome, decompensated chronic liver disease, acute liver failure, graft dysfunction after liver transplantation, liver failure after liver surgery, secondary liver failure, multi organ failure or intractable pruritus in cholestasis, including also hepatic encephalopathy (HE), also known as portosystemic encephalopathy, which is a result of liver failure and characterized by the occurrence of confusion, altered level of consciousness, and coma. Liver dialysis is similar to hemodialysis and based on the same principles, but is also different because it has to address different challenges in comparison to hemodialysis performed on renal patients. Liver dialysis is generally more complex than renal dialysis which is reflected in a more complex device for performing such therapy. Liver dialysis can also be described as a form of artificial extracorporeal liver support.

The so-called hepatorenal syndrome (HRS) is a life-threatening medical condition that consists of rapid deterioration in kidney function in individuals with cirrhosis or massive liver failure. HRS is usually fatal unless a liver transplant is performed, although various treatments, such as dialysis, can prevent advancement of the condition. HRS can affect individuals with cirrhosis (regardless of cause), severe alcoholic hepatitis, or massive hepatic failure, and usually occurs when liver function deteriorates rapidly because of an acute injury such as an infection, bleeding in the gastrointestinal tract, or overuse of diuretic medications. HRS is a relatively common complication of cirrhosis, occurring in 18% of cirrhotics within one year of their diagnosis, and in 39% of cirrhotics within five years of their diagnosis. Deteriorating liver function is believed to cause changes in the circulation that supplies the intestines, altering blood flow and blood vessel tone in the kidneys. The renal failure of HRS is a consequence of these changes in blood flow, rather than direct damage to the kidney. Two forms of hepatorenal syndrome have been defined: Type 1 HRS entails a rapidly progressive decline in kidney function, while type 2 HRS is associated with ascites (fluid accumulation in the abdomen) that does not improve with standard diuretic medications. For example, the risk of death in hepatorenal syndrome is very high; the mortality of individuals with type 1 HRS is over 50% over the short term. The only long-term treatment option for the condition is liver transplantation. As a short-term treatment option before transplantation, liver dialysis may turn out to be vitally important for the patient.

A critical issue of the clinical syndrome in liver failure is the accumulation of toxins not cleared by the failing liver. Based on this hypothesis, the removal of lipophilic, albumin-bound substances such as bilirubin, bile acids, metabolites of aromatic amino acids, medium-chain fatty acids and cytokines should be beneficial to the clinical course of a patient in liver failure. Said toxins do generally not have to be addressed in renal dialysis.

Figure 2:
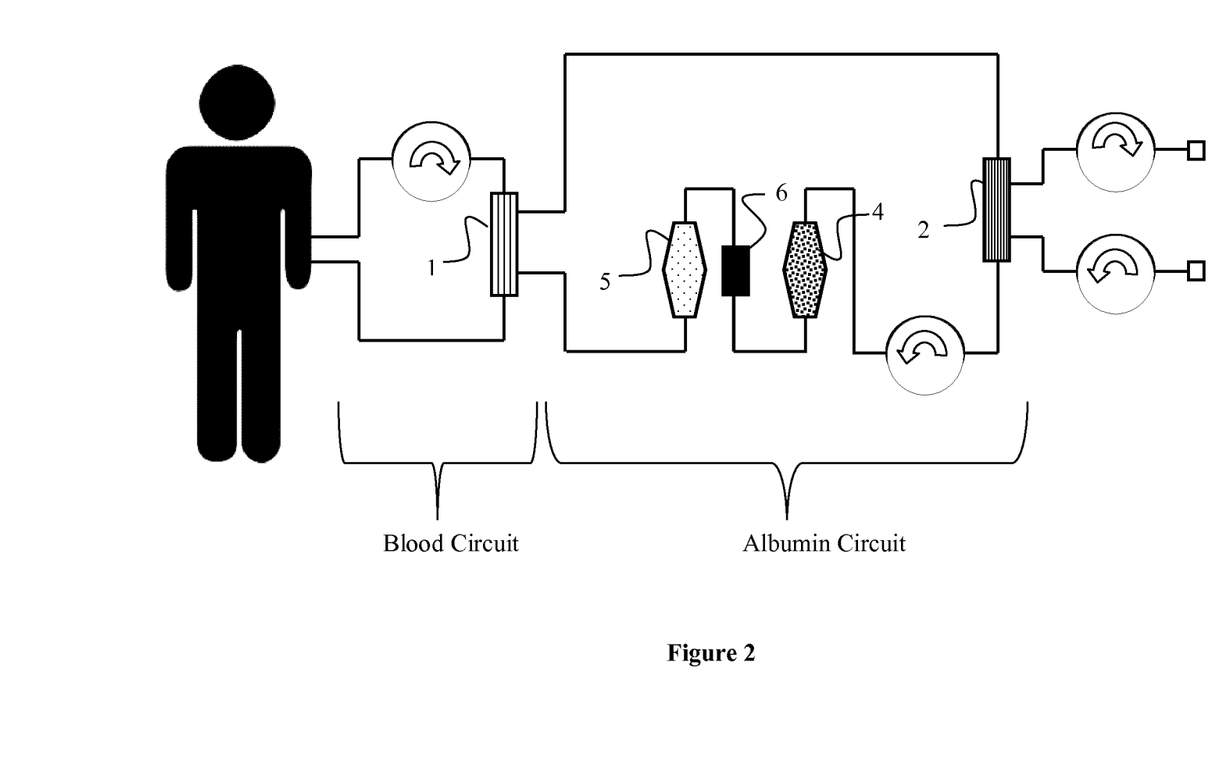
FIG. 2 is a schematic representation of two prior art liver support systems.

A liver dialysis system which has been used for many years to address liver failure is the so-called MARS system (FIG. 2). In the MARS system, blood is cleansed in an extracorporeal circuit that is a combination of both kidney and liver dialysis features. As mentioned before, established methods for kidney dialysis alone are not applicable for addressing liver failure because standard kidney dialysis is restricted to the removal of water-soluble toxins only. The healthy liver, in contrast, also removes essentially hydrophobic, albumin-bound toxins. Albumin is a protein found in the blood that carries water insoluble substances including water insoluble toxins such as mentioned before. For this reason, systems like the MARS system make use of exogenous human albumin to cleanse the blood because the albumin removes the toxins which are bound to the endogenous albumin in the blood that the aqueous solution in kidney dialysis cannot remove, such as unconjugated bilirubin, bile acids, hydrophobic amino and fatty acids. A significant portion of toxins are water-soluble molecules of low- and middle-molecular weight, the concentration of which may be increased by hepatic failure and/or renal failure. These molecules can effectively be removed by a standard renal hemodialysis approach. The MARS system is thus designed to replace the detoxification function of the liver with regard to both water-soluble and water-insoluble albumin-bound toxins. The principles of this system are described, for example, in EP 0 615 780 A1.

The patient's blood in the current MARS system is passed into a hollow fiber membrane hemodialyzer. The dialysate side of the dialyzer provides for clean human albumin that acts as a dialysate. As the patient's blood moves along the membrane, water-soluble and protein bound toxins in the blood are transported through the membrane and into the dialysate albumin solution on the other side. The membrane is impermeable to albumin and to other valuable proteins such as hormones and clotting factors, keeping them in the patient's circulation. The cleansed blood then returns to the patient. Meanwhile, the albumin solution carrying the toxins is recycled by passing first through a low-flux dialyzer. This process removes water-soluble substances from the albumin solution. The albumin then passes through an activated carbon adsorber and, after passing a filter which removes carbon particles, passes through an anion exchanger that removes toxins bound to albumin. The recycled albumin can then again enter the dialyzer and bind again to toxins which can thus be removed from the patient's blood.

A promising approach to further improve the MARS system has been described in WO 2011/131534 A1. In this case the MARS system is modified with regard to the hollow fiber membrane hemodialyzer which receives the patient's blood. Storr et al. have proposed to replace said dialyzer, which is a high-flux hemodialyzer in the MARS system, with a dialyzer comprising a high cut-off type membrane which allows larger molecules to pass the membrane. Molecules which pass the membrane and enter the dialysate which is enriched with albumin also comprise the patient's albumin which carries along toxins bound thereto. That way, more albumin-bound toxins will be transferred and can be removed in the so-called albumin circuit of the MARS system. Still, the MARS system, with regard to the albumin circuit, remains relatively complex and expensive.

It would therefore be desirable to reduce the complexity of the existing liver system and eventually also improve the efficiency of hepatic toxin removal, especially with regard to the elimination of certain unwanted molecules which are closely related to liver failure or impairment, such as unconjugated bilirubin, bile acids and/or IL-6. Generally speaking, it would be especially important to devise a method or device which allows for the simple and efficient removal of protein-bound liver toxins. It is known that the systems which are currently in use have limitations with regard to their elimination performance concerning strongly bound toxins, especially as regards unconjugated bilirubin. Also, the accumulation of pro-inflammatory cytokines in acute liver failure is associated with a high mortality. IL-6, IL-1S and TNF are known to induce massive necrotic inflammation of liver tissue.

A promising approach to simplify the complex available systems which are currently in use in the clinics and, at the same time, to significantly improve their performance has been described in WO 2014/079681 A2. In this system, a first hemodialyzer which does not allow for the passage of an essential amount of albumin over the membrane wall and which mainly serves for removing water-soluble toxins from the blood of a patient is combined, in series, with a second hemodialyzer which receives the cleansed blood from the first dialyzer. The second dialyzer is characterized in that the hollow fibers used therein allow for the passage of significant, but defined amounts of albumin, and that it contains, in its filtrate space, a combination of chemically and/or physically active particulate material which interact with the permeate and binds or adsorbs toxins, including albumin-bound toxins, which have passed the hollow fiber membranes. The cleansed permeate then re-enters the hollow fibers and is combined again with the patient's blood. Accordingly, the second dialyzer described in WO 2014/079681 A2 is arranged in series with a standard hemodialyzer and in direct contact with the patient's blood. The system is thus much less complex than existing approaches for treating liver failure, is highly effective and does not consume exogenous albumin. However, special care needs to be taken to avoid the leakage of the particulate material in case of fiber damage, as both dialyzers are in direct blood contact.

The applicants have now found that it may be beneficial to use the so-called "second dialyzer" or "dialyzer (2)" as it is described in detail in WO 2014/079681 A2, hereinafter referred to as "integrated dialyzer" or "dialyzer (3)", as a component within the MARS system as described before. In the MARS system, the integrated dialyzer replaces several components within the albumin circuit, i.e. the activated carbon adsorber, the filter which removes carbon particles, and the anion exchanger. In doing so, at least two challenges of the systems described before are addressed. The MARS system is considerably simplified because three separate device components can be replaced by only one device. At the same time, the integrated dialyzer is not in contact with blood directly, but is perfused only with the dialysate of the low-flux hemodialyzer as used in the MARS® system. The dialysate, which comprises albumin and toxins bound thereto, is cleansed by the integrated dialyzer as described, for example, in WO 2014/079681 A2. This way, safety as regards transferring particles from the filtrate space into the blood stream is further increased. In addition, it was found that the efficacy of the albumin regeneration may be higher than in a setup where the integrated dialyzer is located in the blood stream, because the sieving coefficient for albumin in the albumin circuit is higher than in a setup where the device is perfused with whole blood or plasma. The device covered by the present invention is simple and able to dispense with plasma fractionation and isolated components such as adsorber cartridges, and at the same time achieves an improved elimination performance for a variety of liver toxins.

According to the present invention, the patient's blood is perfused in a first step through a standard hemodialyzer (1), such as, for example, a high-flux dialyzer as it is known in the art (FIG. 1). This first step serves for removing water-soluble as well as protein-bound, hydrophobic toxins from the blood of the patient. The toxins are transferred to the dialysate side of the dialyzer, which is characterized by the presence of exogenous albumin in the dialysis solution. The dialysate which then carries the water-soluble toxins as well as those toxins which have been bound by the free, exogenous albumin is then perfused through the hollow fiber membranes of a low-flux dialyzer (2) which is focused on the removal of water-soluble toxins contained in the dialysate of the first dialyzer, but does not allow for any passage of albumin over the membrane wall. In a next step, the dialysate which has been cleansed from the water-soluble toxins but still contains toxin-carrying albumin and other blood components that could not be removed by the low flux dialyzer, enters the integrated dialyzer. There, dialysate together with said toxins can pass through the hollow fiber membranes into the filtrate space of the dialyzer and is contacted with certain adsorbents which populate the filtrate space of the device. The material serves to immobilize and thus remove protein-bound toxins and other toxins, all of which can be generically referred to as "hepatic toxins". The filtrate space is in fluid communication only with the lumen space of the hollow fibers. Accordingly, all components which were not adsorbed or bound by the particulate material in the filtrate space will again enter the lumen space of the hollow fibers and leave the dialyzer together with the cleansed albumin and can then be returned to the high-flux dialyzer where new toxins can be received.

Integrated dialyzers which comprise particulate material on the filtrate side are known in the art. Examples for devices which make use of this principle and which can be used according to the invention have been described, for example, in WO 2014/079680 A1 and in WO 2014/079681 A2.

SUMMARY

The present invention is directed to a new liver support system for the treatment of liver failure (FIG. 1). The liver support system is an extracorporeal system for conducting dialysis on a patient suffering from liver failure. The system can be defined as consisting of a blood circuit and an albumin circuit. The blood circuit is characterized by comprising the blood carrying components of the system, whereas the albumin circuit is characterized by comprising components without direct blood contact, including dialyzers (2) and (3), but is in contact with albumin-enriched fluids.

The system is otherwise characterized in that it comprises a dialyzer (1) in the blood circuit into which blood is passed and wherein the filtrate side of the dialyzer (1) is perfused, in opposite direction, with a dialysate solution comprising clean human albumin (FIG. 1). Dialyzer (1) is the interface between the blood and the albumin circuit. According to one embodiment of the invention, dialyzer (1) is a high-flux dialyzer. According to another embodiment of the invention, dialyzer (1) is a high cut-off dialyzer. A high-flux hollow fiber membrane dialyzer (1) does not allow for the passage of essential amounts of albumin over the membrane wall of the hollow fibers which are perfused with the patient's blood, whereas a high cut-off hollow fiber membrane dialyzer allows for the passage of certain amounts of albumin over the membrane wall.

The system further comprises, in its albumin circuit (FIG. 1), a low-flux hollow fiber membrane dialyzer (2) for the removal of water-soluble toxins. Dialyzer (2) receives the albumin containing dialysate from dialyzer (1) which is loaded with toxins from the patient's blood, and passes it through the hollow fiber membranes contained in the dialyzer. Dialyzer (2) is perfused on the filtrate side of the dialyzer, with a buffered aqueous solution in opposite direction. The albumin containing dialysate which has been cleansed from water-soluble toxins is passed on to an integrated hollow fiber membrane dialyzer (3), where it enters the lumen of the hollow fiber membranes contained therein. The filtrate side of dialyzer (3) is in fluid connection only with the lumen of the hollow fiber membranes and is filled with adsorbent material capable of binding to or adsorbing hepatic toxins which could not be cleared by dialyzer (2), specifically protein-bound toxins. The hollow fiber membrane of dialyzer (3) is designed to allow for the passage of certain amounts of albumin which can enter the filtrate space together with toxins bound thereto. Upon adsorption or binding of the said toxins to the adsorbent material, the free albumin again enters the lumen of the hollow fibers of dialyzer (3) and together with the cleansed dialysate is returned to hollow fiber dialyzer (1) for further use as dialysis solution.

The present invention is also directed to the use of a liver support system according to the invention for the removal of hepatic toxins from fluids in extracorporeal therapies.

BRIEF DESCRIPTION OF THE DRAWINGS

FIG. 1 is a schematic representation of the essential components of the liver support system of the invention, wherein hollow fiber membrane dialyzer (1) receives the blood of the patient. Dialyzer (1) can be either a high-flux or a high cut-off dialyzer. The dialysis solution which perfuses dialyzer (1) in opposite direction to the blood is enriched with human albumin (exogenous albumin) which is able to bind protein-bound toxins which pass the membrane wall of dialyzer (1). Dialyzer (2) is a low flux dialyzer which receives the dialysate of dialyzer (1). On the dialysate (filtrate) side, dialyzer (2) is perfused with a buffered aqueous solution in opposite direction to the albumin containing dialysate of dialyzer (1) which flows through the lumen of the hollow fibers. Dialyzer (2) serves for the removal of water-soluble toxins from the dialysate of dialyzer (1). Integrated dialyzer (3) receives the albumin containing retentate of dialyzer (2) from which small water-soluble toxins have been removed. Dialyzer (3) comprises high cut-off type hollow fiber membranes which allow for the passage of a certain defined amount of albumin into the filtrate space of the dialyzer which is populated with one or more adsorbents. The adsorbents serve for binding or adsorbing further toxins, including otherwise protein-bound toxins. The filtrate space of dialyzer (3) is in fluid communication only with the lumen of the hollow fiber membranes which is perfused with the albumin containing fluid. Cleansed fluid, comprising free albumin, will re-enter the hollow fiber membranes of dialyzer (3) and will be returned to dialyzer (1) where it again serves as dialysis solution for accepting protein-bound toxins from the blood of the patient. The dialysis machine which is connected to dialyzer (2) is depicted in FIG. 2 as component (7).

FIG. 2 depicts the so-called MARS® system, wherein a high-flux type hollow fiber membrane dialyzer (1) receives the blood of a patient. The dialyzer does not allow for the passage of essential amounts of albumin over the membrane wall. The dialysis solution which perfuses dialyzer (1) in opposite direction to the blood is enriched with human albumin (exogenous albumin) which is able to bind protein-bound toxins from the blood of the patient. The albumin enriched solution now carrying the toxins is recycled by passing it first through low-flux dialyzer (2) wherein water-soluble substances are removed from the albumin solution. The albumin solution then passes through an activated carbon adsorber (4) and, after passing a filter (6) which removes carbon particles, passes through an anion exchanger (5) which removes further toxins from the fluid. The recycled albumin solution again enters dialyzer (1) and can bind to toxins from patients' blood. The dialysis machine which is connected to dialyzer (2) is depicted in FIG. 2 as component (7). Another system has been described in further detail in WO 2014/079681 A2. This system makes use of the same dialyzer design as regards dialyzer (3) of FIG. 1. However, dialyzer (3) in this approach is not part of an albumin circuit where it is perfused with an albumin enriched dialysate of dialyzer (2) as shown there, but is perfused directly with the blood of the patient. Dialyzer (3) is followed in line by another dialyzer (1), which is a high-flux type dialyzer for removing toxins, such as water-soluble toxins, which have not been cleared from the blood in dialyzer (3). The dialysis machine which is connected to dialyzer (1) is depicted as component (7).

DETAILED DESCRIPTION

The present invention is directed to a liver support system (FIG. 1) for the treatment of a patient suffering from liver failure. The system comprises a blood circuit and an albumin circuit. The blood circuit is characterized by comprising the blood carrying components of the system, whereas the albumin circuit is characterized by comprising components without direct blood contact, including dialyzers (2) and (3), but is in contact with albumin-enriched fluid.

The system is otherwise characterized in that it comprises a hollow fiber membrane dialyzer (1) in the blood circuit into which blood is passed from the patient and wherein the filtrate side of the dialyzer (1) is perfused, in opposite direction, with a dialysate solution comprising clean, exogenous human serum albumin (HAS). For example, the MARS® system makes use of a high-flux membrane which is a blend of polyethersulfone, polyvinyl pyrrolidone and polyamide (MARS®Flux). Conventionally, liver dialysis systems like the ones described here comprise a high-flux dialyzer membrane with a molecular weight cut-off of about 15 to 20 kDa in the presence of whole blood. Such high-flux hollow fiber membrane dialyzer does not allow for the passage of essential amounts of albumin over the membrane wall of the hollow fibers which are perfused with the patient's blood. However, it allows for the passage of toxins from the blood of the patient to the albumin-enriched dialysis fluid on the other side of the membrane. Said hepatic toxins are transported through the membrane and into the dialysate albumin solution on the other side, which marks the passage into the albumin circuit. Protein-bound toxins will be accepted by the free albumin in the dialysis fluid. The cleansed blood returns to the patient. Alternatively, instead of a high-flux type dialyzer, it is also possible to use a dialyzer which comprises a high cut-off membrane, as described, for example, in WO 2011/131534 A1.

The concentration of the HSA in the albumin circuit may vary. In general, it will be in the range of 1% to 25% by weight. According to one embodiment of the invention, the HSA concentration lies in the range of 2% to 20% by weight. According to yet another embodiment of the invention, the HSA concentration lies in the range of 5% to 20% by weight. Liver dialysis systems like the MARS® system are preferably run with a HSA concentration of 10%-25%. HSA concentration may lie in the range of from 5% to 12%, however, if a system according to the invention is used in conjunction with a high cut-off type membrane in dialyzer (1).

The system further comprises, in its albumin circuit, a low-flux hollow fiber membrane dialyzer (2) for the removal of water-soluble toxins. An example for such low-flux dialyzer is the diaFLUX 1.8 dialyzer used in the current MARS® system, even though other low-flux dialyzers, including those which are commercially available, can be used. Dialyzer (2) receives the albumin containing dialysate loaded with toxins from dialyzer (1) and passes it through the lumen of the hollow fiber membranes contained in dialyzer (2). Dialyzer (2) is perfused on the filtrate side of the dialyzer, with a buffered aqueous solution in opposite direction. The albumin containing dialysate of dialyzer (1) is thus cleansed from water-soluble toxins and is then passed on to an integrated hollow fiber membrane dialyzer (3), where it enters the lumen of the hollow fiber membranes contained therein. The filtrate side of dialyzer (3) is in fluid connection only with the lumen of the hollow fiber membranes and is filled with adsorbent material capable of binding or adsorbing various hepatic toxins, including protein-bound hepatic toxins. The hollow fiber membrane of dialyzer (3) is designed to allow for the passage of certain amounts of albumin which enters the filtrate space together with toxins bound thereto. Upon adsorption or binding of the said toxins to the adsorbent material, the free albumin again enters the lumen of the hollow fibers of dialyzer (3) and together with the cleansed fluid is returned to hollow fiber dialyzer (1) for further use as dialysis solution.

In contrast to the MARS system (FIG. 2), the system according to the invention can dispense with the adsorber cartridges (4) and (5) and with filter (6) as separate components, because dialyzer (3) is an integrated device which covers all functions of the said components of the albumin circuit. This entails a significantly reduced complexity in comparison to the MARS system, as well as an easier handling of the system in the clinics and reduced costs. Another improvement compared to the current MARS system as shown in FIG. 2 was found to be a reduced pressure drop in the system due to using hollow fiber based devices instead of adsorber cartridges, which allows for higher flow rates and, consequently, for an improved mass transfer of all substances. Therefore, reduced complexity and costs come with an increased efficacy of the system as regards removing hepatic toxins. As regards the prior art liver support system according to FIG. 2, the system according to the invention was found to have certain advantages. As dialyzer (3) is not part of the blood circuit, the system can, for example, dispense with additional safeguards for preventing leakage of particulate material from the filtrate side of dialyzer (3) into the blood of the patient in case of fiber damage.

The expression "dialysate" as used herein refers to the fluid and components contained therein that passes through a dialysis membrane; the material that does not pass through the membrane and is retained is herein referred to as the "retentate". The "dialysate" can also be referred to as "filtrate".

The expression "protein-bound toxin(s)" refers to hepatic toxins having low water solubility which are mainly bound to proteins when they are present in the serum. Examples for said toxins comprise, but are not limited to, p-cresol, indoxyl sulfate, phenol, homocysteine, and specifically bilirubin and bile acids in case of liver failure. Serum albumin is the most important binding protein for ligands such as bilirubin and bile acids.

In the context of the present invention, the expression "essential amounts of albumin" or "certain amounts of albumin" means, with regard to the hollow fiber membranes of dialyzer (3), that the membrane allows for the passage of albumin with a sieving coefficient measured according to ISO8637 with bovine plasma (protein level 60 g/l), 37° C., $Q_B$ max (generally between 200 and 500 ml/min) and UF 20%, of between 0.1 and 0.3. Thus, the albumin together with the liver toxins which may be bound thereto will get into contact with the particulate material in the filtrate space, whereby said toxins can effectively be immobilized and thus removed. At the same time, the specific hollow fiber membrane which is used in dialyzer (3) prevents the passage of still larger proteins such as, for example, coagulation factors such as fibrinogen and other components which should be retained in the blood of the patient.

If a high-flux dialyzer is used as dialyzer (1), the hollow fiber membrane does not allow for the passage of essential amounts of albumin over the membrane wall, which in this case means that the sieving coefficient for albumin as measured according to ISO8637 with bovine plasma (protein level 60 g/l), 37° C., is below 0.01 at $Q_B$max and UF20%. If a high cut-off dialyzer is used as dialyzer (1), the hollow fiber membrane allows for the passage of certain amounts of albumin over the membrane wall, which in this case means that the sieving coefficient for albumin as measured according to ISO8637 with bovine plasma (protein level 60 g/l), 37° C., is between 0.1 and 0.3 at $Q_B$max and UF20%.

As used herein, the term "sieving coefficient (S)" refers to the physical property of a membrane to exclude or let pass molecules of a specific molecular weight. The sieving coefficient in whole blood, plasma or water can be determined according to standard ISO8637, 2010. Put simply, the sieving coefficient of a membrane is determined by pumping a protein solution (e.g. bovine or human plasma) under defined conditions through a membrane bundle and determining the concentration of the protein in the feed, in the retentate and in the filtrate. If the concentration of the protein in the filtrate is zero, a sieving coefficient of 0% is obtained. If the concentration of the protein in the filtrate equals the concentration of the protein in the feed and the retentate, a sieving coefficient of 100% is obtained.

The hollow fiber membrane dialyzers (1) and (2) which are used in the liver support system according to the invention may be dialyzers as currently used for standard hemodialysis in the treatment of chronic renal dialysis patients. Such dialyzers are high-flux dialyzers and low-flux dialyzers, respectively. Low-flux dialyzers are generally characterized by a lower permeability compared to high-flux membranes.

Low-flux membranes as used in dialyzer (2) can be characterized by having an UF coefficient of below 15 mL/h/mm Hg and a ß2-microglobulin clearance of below 10 ml/min. Based on dextran sieving coefficients, low-flux membranes may further be characterized by a molecular weight cut-off (MWCO) of 10-20 and a molecular weight retention onset (MWRO) of between 2 and 4 kD. The MWRO is defined as the lowest molecular weight for which the sieving coefficient is 0.9. The water permeability of low-flux membranes generally is in the range of from $2\text{-}5 \cdot 10^{-4}$ cm/(bar·s) (with 0.9 wt.-% NaCl at 37±1° C. and $Q_B$ 100-500 ml/min).

According to one embodiment of the invention, the hollow fiber membranes which can be used in a hollow fiber membrane dialyzer (1) are so-called high-flux membranes. High-flux membranes are generally characterized by their higher permeability compared to low-flux membranes, which increases the in vitro clearance of certain marker molecules such as vitamin B12 having a molecular weight of about 1.4 kD. High-flux membranes are also characterized by their ability to remove solutes of higher molecular weight, such as β2-microglobulin (11.8 kD). In the context of the present invention, the term "high-flux" and "high-flux membrane", respectively, refers to membranes having an UF coefficient of >15 mL/h/mm Hg, wherein the UF coefficient determines quantity of pressure that must be exerted across dialysis membrane (transmembrane pressure) to generate a given volume of ultrafiltrate per unit time, a ß2-microglobulin clearance of >20 mL/min, preferably between 20 to 40 mL/min as measured in conventional HD with $Q_B$ 300-400 ml/min and $Q_D$ 500 ml/min for membrane areas between about 1.7 and 2.1 m², and a mass transfer coefficient ($K_oA$) of >450 mL/min. A high-flux membrane in the context of the present invention is further defined by a water permeability of the membrane of $40\text{-}90 \cdot 10^{-4}$ cm/(bar·s) (with 0.9 wt.-% NaCl at 37±1° C. and $Q_B$ 100-500 ml/min). The albumin loss of a high-flux membrane in the context of the present invention is <0.5 g in conventional HD, after 4 h and $Q_B$ of 250 ml/min and $Q_D$ 500 ml/min. High-flux membranes are further characterized by a pore radius of about 3.5-5.5 nm compared to low-flux membranes with a pore radius of about 2-3 nm and high cut-off membranes with a pore radius 8-12 nm, as based on dextran sieving coefficients determined as described, for example, in WO 2015/118045 A1. Based on said dextran sieving coefficients, high-flux membranes may further be characterized by a molecular weight cut-off (MWCO) (kg/mol) of 25-65 and a molecular weight retention onset (MWRO) of between 5 and 10 kD (see also Boschetti-de-Fierro et al. (2013): "Extended characterization of a new class of membranes for blood purification: The high cut-off membranes", *Int J Artif Organs* 36(7), 455-463). High-flux dialyzers can be made from various materials, comprising cellulosic and synthetic materials.

According to one embodiment of the present invention, the high-flux membrane of hollow fiber membrane dialyzers (1) is comprised of at least one hydrophobic polymer and at least one hydrophilic polymer. According to one embodiment of the invention, the hydrophobic polymer is chosen from the group consisting of polyarylethersulfone (PAES), polypropylene (PP), polysulfone (PSU), polycarbonate (PC), polyacrylonitrile (PAN), polyamide (PA) polytetrafluorethylene (PTFE) or combinations thereof, and the at least one hydrophilic polymer is chosen from the group consisting of polyvinylpyrrolidone (PVP), polyethyleneglycol (PEG), polyvinylalcohol (PVA), and copolymer of polypropyleneoxide and polyethyleneoxide (PPO-PEO).

According to yet another embodiment of the invention, high-flux membranes used in hollow fiber membrane dialyzer (1) are comprised of a copolymer of acrylonitrile and sodium methallyl sulfonate and are optionally coated, on their surface, with polyethyleneimine (PEI), preferably high molecular weight PEI, and may further optionally have grafted thereon heparin.

According to one specific embodiment of the invention, dialyzer (1) comprises a membrane based on polyethersulfone, polyamide, and polyvinylpyrrolidone having an asymmetric 3-layer structure and showing a hydraulic permeability (Lp) of about $5\times10^{-4}$ cm/bars. Such membrane is contained, for example, in filters sold by Gambro Lundia AB under the trade name Polyflux® P21L. Another example for a fiber that can be used in a dialyzer (1) according to the present invention is a membrane comprising polyethersulfone, polyamide, and polyvinylpyrrolidone having an asymmetric 3-layer structure and showing a hydraulic permeability Lp of about $80\times10^{-4}$ cm/bars. Such membrane is contained, for example, in filters sold by Gambro Lundia AB under the trade name Polyflux® P210H. Another example for a fiber that can be used in a dialyzer (1) according to the invention is a membrane comprising polyarylethersulfone and polyvinylpyrrolidone and having an asymmetric 3-layer structure and showing a hydraulic permeability (Lp) of about $80 \times 10^{-4}$ cm/bars. Such membrane is contained, for example, in filters sold by Gambro Lundia AB under the trade name Polyflux® Revaclear. According to yet another embodiment of the invention, the liver support system of the invention comprises, as dialyzer (1), the oXiris™ dialyzer (Gambro Lundia AB), comprising a membrane based on a copolymer of acrylonitrile and sodium methallyl sulfonate, which has a homogeneous gel-structure and is coated with polyethyleneimine and heparin, also available from Gambro. According to a yet another embodiment of the invention, a membrane that can be used in the device of the present invention is a membrane also made from a copolymer of acrylonitrile and sodium methallyl sulfonate, which has a homogeneous gel-structure and is contained in filters sold under the trade name Filtral® (Gambro Lundia AB). According to yet another embodiment of the invention, the liver support system of the invention comprises, as dialyzer (1), the Nephral®ST dialyzer, comprising a membrane based on a copolymer of acrylonitrile and sodium methallyl sulfonate, also available from Gambro. According to still another embodiment of the invention, the liver support system of the invention comprises, as dialyzer (1), the Evodial® dialyzer, comprising a membrane based on a copolymer of acrylonitrile and sodium methallyl sulfonate, which has a homogeneous gel-structure and is coated with polyethyleneimine and heparin, also available from Gambro. According to still another embodiment of the invention, the liver support system of the invention may also comprise, as dialyzer (1), dialyzers sold by Fresenius Medical Care as FX 80 and FX 100, both comprising the so-called Helixone® membrane, or the Optiflux® dialyzers F180NR or F200NR, dialyzers sold by Baxter Healthcare Corporation as Xenium XPH 210 or Xenium XPH 190, the ELISIO™ dialyzer sold by Nipro Medical Corporation or dialyzers sold by Asahi Kasei Medical Co. as Rexeed-18S and Rexeed-21S. Methods of producing high-flux and/or low-flux membranes such as mentioned before are known in the art and have been disclosed, for example, in EP 2 113 298 A1 or U.S. Pat. No. 5,891,338 A.

According to another embodiment of the invention, dialyzer (1) comprises a high cut-off membrane. Such high cut-off membranes can be characterized, for example, by a molecular weight cut-off (MWCO) in water, based on dextran sieving coefficients, of between 170 and 320 kD and a molecular weight retention onset (MWRO) in water, based on dextran sieving coefficients, of between 15 and 20 kD. For further details and an overview of various membrane types and their characterization by means of MWCO and MWRO, reference is made again to Boschetti-de-Fierro et al. (2013). The molecular weight retention onset (MWRO) is used for characterizing membranes better than just by a MWCO. The MWRO is defined as the molecular weight at which the sieving coefficient is 0.9. It is analogous to the MWCO and describes when the sieving coefficient starts to fall from 1 to 0. Defining two critical points on the sieving curve for a given membrane allows a better characterization of the sigmoid curve, giving an indication of the pore sizes and also of the pore size distribution. The expression "molecular weight rejection onset" or "MWRO" or "nominal molecular weight rejection onset", as used herein, therefore refers to the molecular mass of a solute where the membranes have a rejection of 10%, or, in other words, allow passage of 90% of the solute, corresponding to a sieving coefficient of 0.9. High cut-off membranes can be further characterized by their pore radius. The pore radius of high cut-off membranes is generally in the range of from 8 to 12 nm. The albumin loss of high cut-off membranes measured in conventional hemodialysis after a 4 hour session with QB 250 ml/min and QD 500 ml/min, for membrane areas between 1.7 and 2.1 m², is generally up to 28 g, compared to an albumin loss of below 0.5 g during the same hemodialysis session with a high-flux dialyzer. The average albumin loss per hour (±20%) is about 7 g for a membrane as used in the Theralite® dialyzer. A high cut-off membrane can further be characterized in that it allows passage of substances having a molecular weight of up to 45 kD with a sieving coefficient measured in whole blood of between 0.1 and 1.0 according to ISO8637 with bovine plasma (protein level 60 g/l), 37° C., at $Q_B$max and UF20%. According to another embodiment of the invention, a high cut-off hollow fiber membrane can be characterized by a sieving coefficient for albumin, measured in bovine blood plasma, of between 0.1 and 0.3 according to ISO 8637 at 37° C., protein level 60 g/l, $Q_B$ max and UF 20%.

A high cut-off membrane according to the invention is comprised of at least one hydrophobic polymer and at least one hydrophilic polymer. According to one embodiment of the invention, the hydrophobic polymer is chosen from the group consisting of polyarylethersulfone (PAES), polypropylene (PP), polysulfone (PSU), polycarbonate (PC), polyacrylonitrile (PAN), polyamide (PA) polytetrafluoroethylene (PTFE) or combinations thereof, and the at least one hydrophilic polymer is chosen from the group consisting of polyvinylpyrrolidone (PVP), polyethyleneglycol (PEG), polyvinylalcohol (PVA), and copolymer of polypropyleneoxide and polyethyleneoxide (PPO-PEO). According to another embodiment of the invention, a high cut-off membrane is comprised of a hydrophobic polymer chosen from the group consisting of polyarylethersulfone (PAES) and polysulfone (PSU) and a hydrophilic polymer chosen from the group consisting of polyvinylpyrrolidone (PVP), polyethyleneglycol (PEG) and polyvinylalcohol (PVA). In yet another embodiment of the invention, a high cut-off membrane is comprised of a hydrophobic polymer chosen from the group consisting of polyarylethersulfone (PAES) and polysulfone (PSU) and the hydrophilic polymer polyvinylpyrrolidone (PVP). Dialyzers comprising high cut-off membranes which are currently on the market are, for example, HCO1100®, septeX™ and Theralite®, all available from Gambro Lundia AB.

The hollow fiber membrane dialyzer (3) which is used in the liver support system according to the invention is characterized in that it comprises a cylindrical filter housing, wherein a bundle of essentially parallel hollow fiber membranes are distributed longitudinally within the housing, a filtrate space, which is in fluid connection only with the lumen of the hollow fiber membranes and, optionally, also with an inlet means and an outlet means. The filtrate space of dialyzer (3) is populated with particulate material which comprises at least one adsorbent for hepatic toxins. The hollow fiber membrane of dialyzer (3) is characterized in that it is a high cut-off membrane as described in detail above in connection with dialyzer (1). An integrated dialyzer (3) as described herein is known and has been described in detail in WO 2014/079680 A1 and WO 2014/079681 A2.

As described above, the high cut-off hollow fiber membrane of dialyzer (3) allows a certain amount of albumin to pass the membrane wall and get in contact with the particulate material which populates the filtrate space of the dialyzer. The albumin, in the context of the present invention, may carry liver toxins which will be removed at least step-wise upon contact with the particulate material in the filtrate space. It is obvious that other not protein-bound liver toxins may also pass the membrane wall and may be adsorbed by or bound to the particulate material. The cleansed permeate comprising also albumin with essentially no toxins bound thereto can leave the filtrate space by re-entering the lumen space of the hollow fiber membranes and leave the dialyzer. A given molecule, such as albumin, may of course pass the membrane wall more than once during its passage through dialyzer (3) and may thus have more than one opportunity to contact the particulate material whereby bound toxins may be removed.

The manufacturing of low-flux, high-flux and high cut-off hollow fiber membranes as used in dialyzers (1), (2) and/or dialyzer (3) according to the invention, are known in the art. The process generally follows a phase inversion process, wherein a polymer or a mixture of polymers is dissolved in a solvent to form a polymer solution. The solution is degassed and filtered and is thereafter kept at an elevated temperature. Subsequently, the polymer solution is extruded through an outer ring slit of a nozzle having two concentric openings. Simultaneously, a center fluid is extruded through an inner opening of the nozzle. At the outlet of the spinning nozzle, the center fluid comes in contact with the polymer solution and at this time the precipitation is initialized.

The precipitation process is an exchange of the solvent from the polymer solution with the non-solvent of the center fluid. By means of this exchange the polymer solution inverses its phase from the fluid into a solid phase. In the solid phase the pore structure, i.e. asymmetry and the pore size distribution, is generated by the kinetics of the solvent/non-solvent exchange. The process works at a certain temperature which influences the viscosity of the polymer solution. The temperature at the spinning nozzle and the temperature of the polymer solution and center fluid may vary and influences the resulting membrane type. The viscosity determines the kinetics of the pore-forming process through the exchange of solvent with non-solvent. Subsequently, the membrane is preferably washed and dried. By the selection of precipitation conditions, e. g. center fluid composition, temperature and speed, the hydrophobic and hydrophilic polymers are "frozen" in such a way that a certain amount of hydrophilic end groups are located at the surface of the pores and create hydrophilic domains. The hydrophobic polymer builds other domains. A certain amount of hydrophilic domains at the pore surface area are needed to avoid adsorption of proteins. The size of the hydrophilic domains should preferably be within the range of 20 to 50 nm. In order to repel albumin from the membrane surface, the hydrophilic domains also need to be within a certain distance from each other. By the repulsion of albumin from the membrane surface, direct contact of albumin with the hydrophobic polymer, and consequently the absorption of albumin, are avoided.

The polymer solution used for preparing the membranes as used in dialyzers according to the invention preferably comprises 10 to 20 wt.-% of hydrophobic polymer and 2 to 11 wt.-% of hydrophilic polymer. The center fluid generally comprises 45 to 60 wt.-% of precipitation medium, chosen from water, glycerol and other alcohols, and 40 to 55 wt.-% of solvent. In other words, the center fluid does not comprise any hydrophilic polymer. The polymer solution coming out through the outer slit openings is generally, on the outside of the precipitating fiber, exposed to a humid steam/air mixture. Preferably, the humid steam/air mixture has a temperature of at least 15° C., more preferably at least 30° C., and not more than ° C., more preferably not more than 60° C. Preferably, the relative humidity in the humid steam/air mixture is between 60 and 100%. Furthermore, the humid steam in the outer atmosphere surrounding the polymer solution emerging through the outer slit openings preferably includes a solvent. The solvent content in the humid steam/air mixture is preferably between 0.5 and 5.0 wt-%, related to the water content. The effect of the solvent in the temperature-controlled steam atmosphere is to control the speed of precipitation of the fibers. When less solvent is employed, the outer surface will obtain a denser surface, and when more solvent is used, the outer surface will have a more open structure.

Before extrusion, suitable additives may be added to the polymer solution. The additives are used to form a proper pore structure and optimize the membrane permeability, the hydraulic and diffusive permeability, and the sieving properties. In a preferred embodiment, the polymer solution contains 0.5 to 7.5 wt.-% of a suitable additive, preferably chosen from the group comprising water, glycerol and other alcohols. The solvent may be chosen from the group comprising N-methylpyrrolidone (NMP), dimethyl acetamide (DMAC), dimethyl sulfoxide (DMSO) dimethyl formamide (DMF), butyrolactone and mixtures of said solvents.

Methods for producing suitable high cut-off membranes are disclosed, for example, in WO 2004/056460 A1, WO 2014/079681 A2 or in WO 2011/131534 A1.

According to one embodiment of the invention, the fiber packing density or fiber allocation within dialyzer (3) is in the range of from 15% to 50%. According to another embodiment of the invention, the fiber packing density or fiber allocation within dialyzer (3) is in the range of from 20% to 40%. According to yet another embodiment of the invention, the total membrane area of the dialyzer (2) is in the range of between 1.0 and 2.5 $m^2$. The fibers in the dialyzer preferably are homogenously distributed over the length of the cylindrical housing of the filter module, which means that the distance between the single fibers remains essentially the same over the total length of the fibers. In another embodiment of the invention, the fiber allocation is between 25% and 35%. In the context of the present invention, the fiber packing density is calculated from the percentage of the cross section surface allocated by the fibers per utilizable cross section surface in the filter housing. The utilizable cross section surface corresponds to the cross section surface. The theoretical maximum packing density would thus correspond to an allocation of 100%. In reality, packing densities of up to 70% or 75% can be reached, depending on the fibers used.

The fibers which can be used for producing a module according to the invention can be straight or crimped, wherein crimped fibers are fibers having a certain ondulation which is essentially sinusoidal but may deviate from such sinusoidal ondulation over the length of the fiber, i.e. wavelength and/or amplitude of the crimps of one single fiber or between two or more fibers may be different. Ondulated fibers and methods for ondulating fibers are known in the art and have been described, for example, in EP 1 257 333 A1. It is possible to combine straight and crimped fibers in one device. In one embodiment of the invention, all of the fibers in the filter module are ondulated. According to another embodiment of the invention, all of the fibers in the filter module are straight fibers. For a hollow fiber membrane dialyzer (3) according to the invention, it may be advantageous to use ondulated fibers with an amplitude of between 0.1 mm and 3.0 mm and a wavelength of between 3.5 mm and 11.5 mm. For example, the standard hollow fiber which is used in a Theralite® dialyzer has an amplitude of 0.6 mm and a wavelength of about 7.3 mm.

According to another embodiment of the invention, the membrane surface area of a hollow fiber membrane dialyzer (3) is in the range of from 1.0 to 3.0 m². Generally, a membrane surface area of between 1.3 and 2.7 m² will be sufficient for allowing an effective removal of liver toxins with dialyzer (2) according to the invention. According to yet another embodiment of the invention, the fiber dimensions are in the range of 180-250 µm (inner diameter) and 35-80 µm (wall thickness).

The particulate material used in dialyzer (3) according to the invention may consist of hydrophobic and/or hydrophilic material and is chosen from the group consisting of oxygen-containing adsorbents, carbon-based adsorbents and polymer-based adsorbents or combinations thereof. The expression "adsorption" as it is used herein refers to the preferential partitioning of substances from liquid phase onto the surface of a solid substrate (the particulate material). Physical adsorption is caused mainly by van der Waals forces and electrostatic forces between adsorbate molecules and the atoms which compose the adsorbent surface. Thus adsorbents are characterized first by surface properties such as surface area and polarity. Non-polar adsorbents are generally referred to a as "hydrophobic". Carbonaceous adsorbents, polymer adsorbents and silicalite are typical non-polar adsorbents.

The expression "particulate material" as used herein refers to the material which is filled into and populates the filtrate space of a hollow fiber membrane module or filter. The particulate material is generally referred to, throughout the description, as consisting of particles having a certain average diameter. According to one embodiment of the invention, the particulate material consists of particles having a diameter of between 1 µm to 300 µm.

According to yet another embodiment of the invention, the filtrate space is homogenously populated with a particulate material with a certain filling ratio which is adapted to the particulate material used, the packing density within the housing and the geometry of the housing itself, comprising the available volume of the filtrate space. The expression "homogenous" as used herein means that the particulate material, i.e. the particles it consists of, is evenly distributed over the filtrate space. This means that the average number of particles per volume, for example cm³, is essentially the same over the space. The expression "essentially the same" used in connection with the average number of particles in a cm³ means that the number of particles in a given volume area of 1 cm³ may differ from the number of particles in a second volume area of 1 cm³ by not more than up to 20%, preferably by not more than 10%.

The expression "filling ratio" as used herein, refers to the ratio of the volume in ml of the maximal amount of particulate material, in its dry form or wet form, respectively, which can be accommodated in the filtrate space of a given hollow fiber membrane module ($V_{PM}$) and the utilizable volume in ml of the filtrate space of said module ($V_{FS}$):

$$\text{Filling ratio} = \frac{V_{PM}(\text{ml})}{V_{FS}(\text{ml})}.$$

$V_{PM}$(ml) thus represents the volume of the particulate material which can be accommodated in the filtrate space of the device. $V_{FS}$(ml) represents the utilizable filtrate space, which is known or can easily be determined for a given hollow fiber membrane filter module. A ratio of 1.0 would thus mean that the complete utilizable volume of the filtrate space is occupied by the particulate material. The lower the ratio gets, the less particulate material is present in the filtrate space of the module. The filling ratio always refers to modules wherein essentially the complete utilizable volume of the module has been exhausted. "Exhausted", in the context of the present invention, means that no more particulate material can be filled into the device. $V_{PM}$(ml) can be calculated from the total amount of particulate material in g which can been filled into the module with a given method, divided by the bulk density (g/ml) of the material. The bulk density of a particulate material is defined as the mass of the particles of the material per total volume they occupy. It should be noted that the bulk density of a particulate material can change depending on how the material is treated. For example, the particulate material, simply poured into a cylinder, will have a certain bulk density ("bulk density"). If the cylinder is agitated, the particles will move and usually settle closer together, resulting in a higher bulk density. For this reason, the bulk density of the particulate material in a filter which was prepared according to the invention is referred to as a "tapped density" (ρ), which in principle refers to the bulk density of the particulate material after compaction. For a given material ρ can be determined according to DIN ISO 3953. The maximal bulk density ("tapped density") is reached when no further compaction of the material takes place. The volume $V_{PM}$(ml) of the particulate material which can be accommodated in the filtrate space of a given hollow fiber membrane module can thus be calculated:

$$V_{PM}(\text{ml}) = \frac{m_{PM}(\text{g})}{\rho(\text{g/ml})}.$$

$m_{PM}$ represents the amount of particulate material which could be accommodated in the filtrate space of the module. $m_{PM}$ can be determined for example by subtracting the amount of remaining particulate material (filtered off and dried, in case the material was filled into the module as a suspension) from the initial quantity of (dry) particulate material. According to one aspect of the present invention, dialyzer (3) provides for filling ratios in a range of between 0.6 and 1.0. According to another aspect of the invention, dialyzer (3) provides for filling ratios in a range of between 0.4 and 0.7. According to yet another aspect of the invention, dialyzer (3) provides for filling ratios in a range of between 0.3 and 0.5.

The uncharged or non-polar hydrophobic material for binding and/or adsorbing liver toxins which populates the filtrate space of the hollow fiber membrane dialyzer (2) according to the invention may be chosen from a range of materials which are generally known in the art. According to one aspect of the present invention hydrophobic particulate material is chosen from the group consisting of activated carbon, carbon nanotubes, hydrophobic silica, styrenic polymers, polydivinylbenzene polymers and styrene-divinylbenzene copolymers. Activated carbon can be used, for example, in particulate form as powder or fine granules less than 1.0 mm in size with an average diameter between 0.001 and 0.15 mm or as granular activated carbon with relatively larger particle size compared to powdered activated carbon. Granular activated carbon has the advantage of easier handling and higher safety with regard to its retention in the filtrate space. Activated carbon which may be used in dialyzer (2) according to the invention may be acid washed granular activated carbon particles. According to one aspect of the present invention, the particle size of the granular activated carbon is in the range of from >10 mesh (2.0 mm) and <40 mesh (0.420 mm). According to another aspect of the present invention, particle size of the activated carbon is in the range of about 0.200 mm. The total surface area of activated carbon which may be advantageously used according to the invention is in the range of from 600 $m^2/g$ and 1200 $m^2/g$. Such activated carbon can be purchased, for example, as Norit® GAC 1240 PLUS A (Norit Nederland BV). Examples for polymeric hydrophobic material which can be used, are, for example, styrenic polymers like DOWEX™ OPTIPORE™ L493 and V493 or Amberlite® XAD®-2, polydivinylbenzene polymers or styrene-divinylbenzene copolymers (e.g. Amberlite® XAD4 or Amberchrom™ CG161), poly(1-phenylethene-1,2-diyl) (Thermocole), or hydrophobic silica, which is silica that has hydrophobic groups chemically bonded to the surface, or combinations thereof. Hydrophobic silica can be made both from fumed and precipitated silica. Another hydrophobic material which can be used is known as Ujotit, a copolymer of styrene and divinylbenzene without any functional groups, which is available as Ujotit PA-30, Ujotit PA-40 or Ujotit PA-20. According to one embodiment of the present invention, the particulate material in the filtrate space of dialyzer (2) comprises a copolymer of styrene and divinylbenzene without any functional groups, such as Ujotit PA-30. Ujotit PA-30 particles or beads have an average diameter of between 80-200 μm and a specific surface of between 750-850 $m^2/g$. According to another embodiment of the present invention, the particulate material in the filtrate space of dialyzer (2) comprises activated carbon, such as, for example, Norit® GAC 1240 PLUS A (Norit Nederland BV). According to yet another embodiment of the invention, the particulate material in the filtrate space of dialyzer (2) comprises, as uncharged hydrophobic material, a combination of at least one activated carbon and at least one copolymer of styrene and divinylbenzene without any functional groups.

The charged or polar hydrophilic material for binding and/or adsorbing liver toxins which populates the filtrate space of the hollow fiber membrane dialyzer (2) according to the invention may be chosen from a range of materials which are known in the art. According to another aspect of the present invention, the particulate material may consist of cation exchange particles which may be used without further modification. Such cation exchange material is generally based on matrices of agarose, cellulose, dextran, methacrylate, polystyrene or polyacrylic acid. Such materials are generally known and commercially available, for example, under trade names such as Sepharose® CM, Sephadex, Toyopearl®, Amberlite®, Diaion™, Purolite®, Dowex® and Duolite® $SO_3H$, respectively.

According to another aspect of the present invention, the particulate material may consist of anion exchange material which can be used without further modification. Such anion exchange material may be based on polystyrene or styrene-divinylbenzene and which may be unmodified or modified with sulphonic acids, polyamines or quaternary or tertiary amines. According to one aspect of the invention, the particles are based on a copolymer of styrene and divinylbenzene carrying active groups such as quaternary ammonium groups, dimethylethanolamine groups, dimethylethanolbenzyl ammonium groups, benzyltrialkyl ammonium groups, benzyldimethyl(2-hydroxyethyl) ammonium and/or trimethylbenzyl ammonium functional groups. According to a specific aspect of the present invention, the particles used are based on a copolymer of styrene and divinylbenzene carrying quaternary ammonium groups. According to one aspect of the invention, the copolymer of styrene and divinylbenzene carries trimethylbenzyl ammonium functional groups, which is also referred to as Cholestyramine, Cuemid, MK-135, Cholbar, Cholbar, Questran, Quantalan, Colestyramine or Dowex® 1×2-Cl. Such anion exchange media which can be used are known, for example, under the trade name Amberlite®. Amberlite® comprises, for example, a matrix formed of styrene-divinylbenzene having active or functional groups such as quaternary ammonium groups, benzyldimethyl (2-hydroxyethyl) ammonium groups or dimethylethanolamine groups. Other anion exchange media which can be used are known, for example, under the trade name Dowex®. Dowex® comprises, for example, a matrix formed of styrene-divinylbenzene which may have active or functional groups such as trimethylbenzylammonium. According to one embodiment of the invention, the particulate material in the filtrate space of dialyzer (2) comprises at least one copolymer of styrene and divinylbenzene carrying trimethylbenzyl ammonium functional groups, such as, for example, Cholestyramine, Cuemid, MK135, Cholbar, Cholbar, Questran, Quantalan, Colestyramine, Purolite® or Dowex® 1×2-Cl.

According to yet another embodiment of the invention, the particulate material in the filtrate space of dialyzer (2) comprises a combination of at least one activated carbon, at least one copolymer of styrene and divinylbenzene without any functional groups and at least one copolymer of styrene and divinylbenzene carrying trimethylbenzyl ammonium functional groups. Possible ratios between the respective components are in the range of from 1:1:1 and 10:5:1. According to still another embodiment of the invention, the particulate material in the filtrate space of dialyzer (2) comprises a combination of at least one copolymer of styrene and divinylbenzene without any functional groups and at least one copolymer of styrene and divinylbenzene carrying trimethylbenzyl ammonium functional groups. Possible ratios between the respective components are in the range of from 10:1 to 1:1.

According to one embodiment of the invention, the polymeric particulate material is used in the form of beads, which are small, essentially spherical particles which may differ in size and composition and can have an average diameter in the range of from 100 nm to 5 mm and especially in the range of from 3 μm to 300 μm.

Methods for producing a dialyzer module (3) are known and are described in detail in WO 2014/079680 A1 and WO 2014/079681 A2.

According to one aspect of the invention, the hollow fiber membrane dialyzer (3) is part of an extracorporeal liver support system for the removal of hepatic toxins, which accumulate in incidents of liver failure, including albumin bound toxins, from blood. The treatment differs from hemodialysis in renal failure by the need to remove different types of toxins, including especially protein-bound toxins from the patient's blood. In the context of the present invention, substances which, in the course of liver failure, have been shown to specifically accumulate and/or negatively affect the patient and which need to be removed by a liver support system are referred to as "hepatic toxins" or "liver toxins". Hepatic toxins in the sense of the present invention thus comprise, without limitation, ammonia, mercaptans, phenols, bilirubin, bile acids (e.g. chenodeoxycholic acid), certain vasodilators (e.g. aldosterone, norepinephrine, vasopression, plasma renin), metabolites of aromatic amino acids, lactic acid, urea, uric acid, medium-chain fatty acids and pro- and anti-inflammatory cytokines (e.g. IL6, IL8, IL10, TNFa, sTNFaR1), leukemia inhibitory factor (LIF), liver cell growth inhibitors such as TGF-ß1 and drugs that may cause liver damage or failure (e.g. diazepam, acetaminophen, phenylbutazone) etc. For example, hydrophobic bile acids are cytotoxic at high concentrations and their accumulation within hepatocytes may lead to apoptosis or necrosis. Pro-inflammatory cytokines are believed to mediate hepatic inflammation, apoptosis and necrosis of liver cells, cholestasis, and fibrosis (see, for example, Stauber et al (2010): MARS and Prometheus in Acute-on-Chronic Liver Failure: Toxin Elimination and Outcome. *Transplantationsmedizin* 22:333-338). The treatment of a patient suffering from liver failure with a liver support device according to the invention contributes to reduced blood levels of such hepatic toxins. It should be noted here that toxins which are generally removed during standard renal hemodialysis, and which can be referred to as "renal" or "uremic" toxins (urea etc.) will also be removed by the liver support system by hollow fiber membrane dialyzers (1) and (2). In the context of the present invention, the expression "hepatic toxins" or "liver toxins" generally encompasses such uremic toxins.

The term "liver failure" in the context of the present invention refers to the inability of the liver to perform its normal synthetic and metabolic function as part of normal physiology. Liver failure thus leads, for example, to an insufficient detoxification of albumin, which is followed by an exhaustion of the binding capacity of albumin and an enrichment of the otherwise albumin-bound toxins, e.g. of unconjugated bilirubin. Treatment is indicated, for example, at a bilirubin concentration of >10 mg/dL. However, there are liver disorders where a liver dialysis treatment is indicated, but which is not characterized by increased bilirubin levels. Disorders which are associated with the expression "liver failure" as used in the present invention include, but are not limited to, hepatorenal syndrome, decompensated chronic liver disease, acute liver failure, graft dysfunction after liver transplantation, liver failure after liver surgery, secondary liver failure, multi organ failure, exogenous intoxication or intractable pruritus in cholestasis etc.

It is an advantage of the liver support system according to the present invention that it can be based on the well-established MARS system without major complications, whereas the efficacy of the simplified system can be improved by using the integrated dialyzer (3) in the albumin circuit.

It is known that albumin can be adsorbed, to a certain extent, to the adsorbent which is present in the filtrate space of dialyzer (3). Albumin is synthesized only in the liver. The albumin concentration in plasma in healthy humans usually ranges between 33 and 52 g/l. The normal rate of albumin synthesis is about 0.2 g per kg body weight per day and a steady state exists between albumin synthesis and metabolism. The amount of albumin metabolized daily is believed to be proportional to the plasma concentration, meaning that a fixed percentage of about 10% of plasma albumin content is metabolized per day. The half-life of albumin is inversely proportional to the plasma albumin concentration, that is, a decreased albumin content results in increased half-life, whereas increasing albumin concentrations cause the metabolic rate to increase by up to 50% (Boldt, *Br. J. Anaesth.* (2010) 104 (3): 276-284). Therefore, a substitution of the albumin which may be adsorbed by the adsorbent during the treatment with a liver support system according to the invention may not be necessary. However, substitution of albumin may be indicated especially in cases of spontaneous bacterial peritonitis (SBP), hepatorenal syndrome (HRS), and post-paracentesis syndrome (PPS) due to the fact that the liver is severely compromised. Substitution can be done according to the state of the art, mostly by infusion. Therefore, according to one aspect of the invention, liver support or dialysis treatment according to the invention may be followed by the substitution of albumin which was adsorbed during the treatment in order to maintain a serum albumin level of above 30 g/l.

It will be readily apparent to one skilled in the art that various substitutions and modifications may be made to the invention disclosed herein without departing from the scope and spirit of the invention. The present invention will now be illustrated by way of non-limiting examples of preferred embodiments in order to further facilitate the understanding of the invention.

EXAMPLES

Example 1

Preparation of a Hollow Fiber Membrane Dialyzer (3) Comprising Hollow Fibers and Particulate Material in the Filtrate Space Standard hollow fibers were used to prepare filter modules with active particulate material on the filtrate side of the module. The housings used possess connectors at the blood side and the filtrate side according to ISO 8637:2004. The total membrane surface area was 1.7 $m^2$. The fibers were slightly crimped. The housings had a diameter of 48 mm and a total length (effective fiber length) of 270 mm. The potting material consisted of polyurethane. The total amount of particulate material consisting of hydrophobic adsorber (Purolite) and ion exchanger (cholestyramin) which was introduced into the filtrate space was 56.07 g. The tapped densities these materials can be used to calculate the filling ratio for the modules according to DIN ISO 3953.

Example 2

Removal of Liver Toxins

The liver support system according to the invention (see FIG. 1) was tested in a re-circulating test setup comprising the Prototype of Example 1 as dialyzer (3), see FIG. 1. The test pool of 3000 ml contained 75 mg/l conjugated bilirubin (Sigma) and 25 mg/l unconjugated bilirubin $M_W$ 842.9 (Calbiochem), as well as 100 mg/l chenodeoxycholic acid (CDCA) (Sigma) in Octaplas® LG human plasma (blood group 0, from Octapharma); it was kept at about 37° C. The pool further contained 5 ml heparin (Heparin-Natrium-25000-ratiopharm). 60 ml 0.1M HCl were added to reach a neutral pH. The pool was protected from light at all times. The dialyzers were connected to the machine as prescribed and run in CVVHDF mode. A blood warmer (Prisma-Therm® II) was connected downstream and set to 38° C. The system was flushed with 2×21 NaCl 0.9% comprising 5000 IU/l heparin. $Q_B$=200 ml/min, $Q_D$=1.5 l/h and replacement fluid 1 l/h (total: 2.5 l/h). UF=0 l/h. The system was run for 8 h. After that the filter and bloodlines were flushed with NaCl 0.9%. Samples of 3× 1.5 ml were taken after 0 min, 10 min, 30 min, 60 min, 90 min, 120 min, 2 h, 3 h, 4 h, 4.25 h, 5 h, 6 h, 7 h, 8 h. 1 ml heparin is added after 60 min and then after every other hour. Plasma solution (100 ml) was added after 4 h and 8 h, containing 21.4 mg conjugated bilirubin, 7.1 mg unconjugated bilirubin, and 28.6 mg chenodeoxycholic acid. The dialysis solution used was Prismasol® 2 (Gambro). Flow rates: $Q_B$=200 ml/min; $Q_{Alb}$=250 ml/min; PBP=0 L/h; $Q_D$=1.5 L/h; Replacement: 1.5 L/h; UF=0 L/h.

The samples obtained during the tests were analyzed. The bilirubin samples were evaluated with the Bilirubin Auto Direct FS test kit from DiaSys Diagnostic Systems GmbH, Germany, for conjugated bilirubin, and with the ABX Pentra Bilirubin Total CP test kit from HORIBA ABX SAS, France, for total bilirubin. The CDCA concentrations were determined with the help of the Bile Acid Kit from Trinity Biotech (St. Louis, USA).

Figure 3:
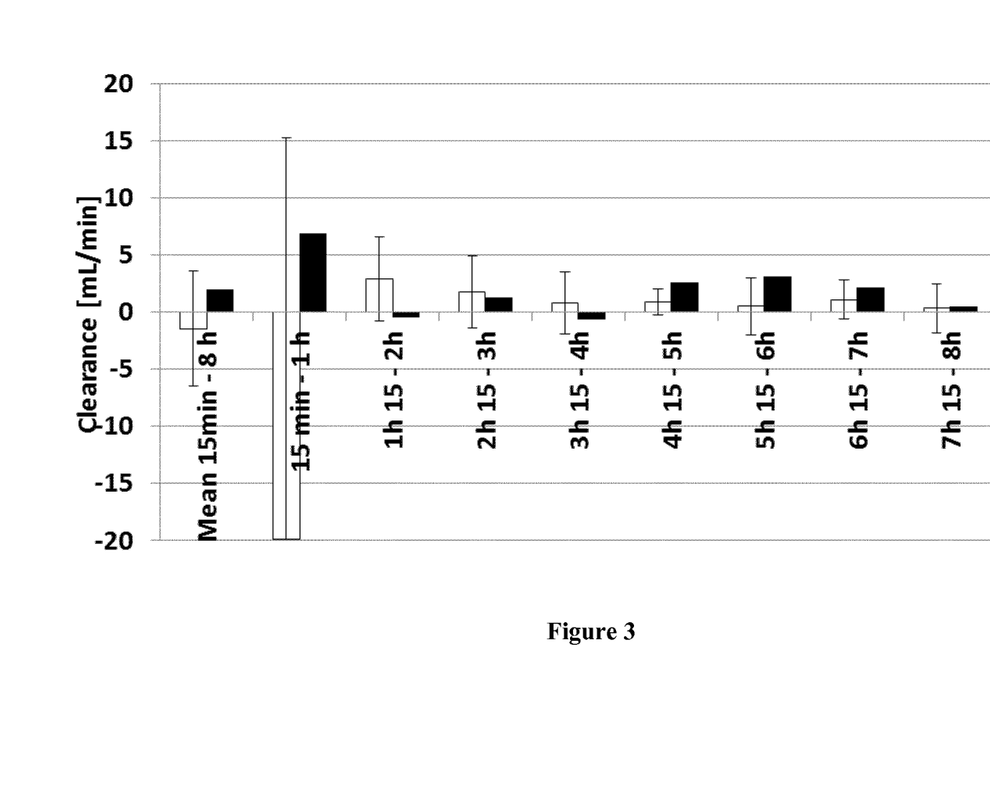
FIG. 3 depicts the results of Example 2, wherein a liver support system according to the invention (see FIG. 1) was tested in a re-circulating test setup comprising the Prototype of Example 1 as dialyzer (3) according to FIG. 1 in comparison with a MARS type set-up (FIG. 2). The test pool of 3000 ml contained 75 mg/l conjugated bilirubin and 25 mg/l unconjugated bilirubin $M_W$ 842.9, as well as 100 mg/l chenodeoxycholic acid (CDCA) in Octaplas® LG human plasma (blood group 0, from Octapharma). The bilirubin total clearance (indirect for better comparison) is maintained or higher in a set-up according to the invention (black bars) in comparison with the set-up as known (white bars).
Figure 4:
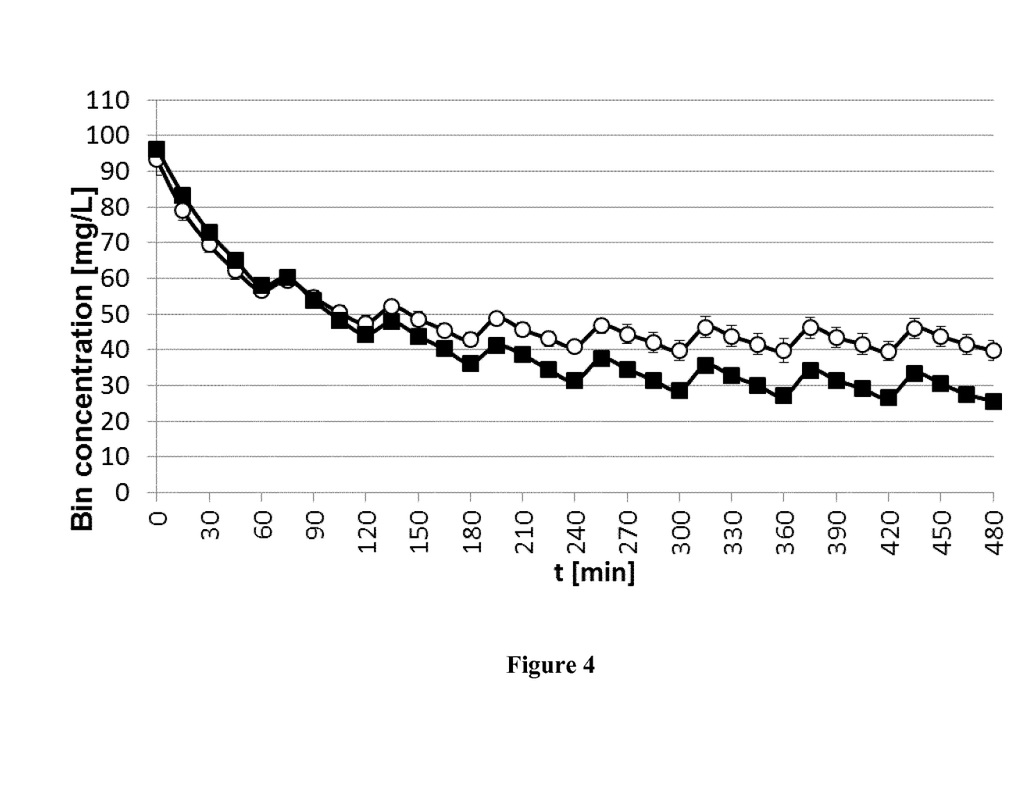
FIG. 4 depicts the results of Example 2, wherein a liver support system according to the invention (see FIG. 1) was tested in a re-circulating test setup comprising the Prototype of Example 1 as dialyzer (3) according to FIG. 1 in comparison with a MARS type set-up (FIG. 2). The test pool of 3000 ml contained 75 mg/l conjugated bilirubin and 25 mg/l unconjugated bilirubin $M_W$ 842.9, as well as 100 mg/l chenodeoxycholic acid (CDCA) in Octaplas® LG human plasma (blood group 0, from Octapharma). The removal chenodeoxycholic acid is in mean 40% higher in a set-up according to the invention (black squares) in comparison with the set-up as known (open circles).

The results for the clearance of conjugated and unconjugated bilirubin as well as for chenodeoxycholic acid (in mg) are shown in FIG. 3 and FIG. 4. In FIG. 3, the bilirubin total clearance is maintained or higher in a set-up according to the invention (black bars, see also FIG. 1) in comparison with the set-up as known (white bars, see also FIG. 2). The chenodeoxycholic acid clearance (FIG. 4) is in mean 40% higher in a set-up according to the invention (black squares) in comparison with the set-up as known (open circles).

The invention claimed is:

1. A device comprising
(a) a first hollow fiber membrane dialyzer comprising a filtrate side
wherein the first hollow fiber membrane dialyzer comprises a high cut-off membrane having a molecular weight cut-off in water, based on dextran sieving coefficients, of between about 170 kD and about 320 kD and a molecular weight retention onset in water, based on dextran sieving coefficients, of between about 15 kD and about 20 kD,
wherein the first hollow fiber membrane dialyzer is configured for perfusion on the filtrate side of the first hollow fiber membrane dialyzer with a dialysate solution in a direction opposite to blood flow within the first hollow fiber membrane dialyzer, and
wherein the dialysate solution comprises human serum albumin (HSA);
(b) a second hollow fiber membrane dialyzer comprising a filtrate side and a lumen side,
wherein the second hollow fiber membrane dialyzer comprises a hollow fiber membrane,
wherein the second hollow fiber membrane dialyzer is configured for receiving the dialysate solution from the first hollow fiber membrane dialyzer,
wherein the second hollow fiber membrane dialyzer is configured for passing the dialysate solution through the lumen side of the second hollow fiber membrane dialyzer, and
wherein the second hollow fiber membrane dialyzer is configured for perfusion on the filtrate side of the second hollow fiber membrane dialyzer with a buffered aqueous solution in a direction opposite to the passing of the dialysate solution through the lumen side of the second hollow fiber membrane dialyzer; and
(c) a third hollow fiber membrane dialyzer comprising a filtrate side, a lumen side, and a filtrate space,
wherein the third hollow fiber membrane dialyzer comprises a hollow fiber membrane,
wherein the filtrate side of the third hollow fiber membrane dialyzer is configured to be in fluid connection only with the lumen side of the third hollow fiber membrane dialyzer,
wherein the lumen side of the third hollow fiber membrane dialyzer is configured for receiving the dialysate solution from the second hollow fiber membrane dialyzer, and
wherein the filtrate space of the third hollow fiber membrane dialyzer comprises at least one adsorbent.

2. A device according to claim 1, wherein the hollow fiber membrane of the second hollow fiber membrane dialyzer is a low-flux membrane having a molecular weight cut-off in water, based on dextran sieving coefficients, of between about 10 kD and about 20 kD and a molecular weight retention onset in water, based on dextran sieving coefficients, of between about 2 kD and about 4 kD.

3. A device according to claim 1, wherein
i) the high cut-off membrane of the first hollow fiber membrane dialyzer comprises A) at least one hydrophobic polymer selected from the group consisting of polyarylethersulfone (PAES), polypropylene (PP), polysulfone (PSU), polycarbonate (PC), polyacrylonitrile (PAN), polyamide (PA), polytetrafluorethylene (PTFE), or combinations thereof and B) at least one hydrophilic polymer selected from the group consisting of polyvinylpyrrolidone (PVP), polyethyleneglycol (PEG), polyvinylalcohol (PVA), and a copolymer of polypropyleneoxide and polyethyleneoxide (PPO-PEO); or
ii) the hollow fiber membrane of the second hollow fiber membrane dialyzer comprises A) at least one hydrophobic polymer selected from the group consisting of polyarylethersulfone (PAES), polypropylene (PP), polysulfone (PSU), polycarbonate (PC), polyacrylonitrile (PAN), polyamide (PA), polytetrafluorethylene (PTFE), or combinations thereof and B) at least one hydrophilic polymer selected from the group consisting of polyvinylpyrrolidone (PVP), polyethyleneglycol (PEG), polyvinylalcohol (PVA), and a copolymer of polypropyleneoxide and polyethyleneoxide (PPO-PEO); or
iii) the hollow fiber membrane of the third hollow fiber membrane dialyzer comprises A) at least one hydrophobic polymer selected from the group consisting of polyarylethersulfone (PAES), polypropylene (PP), polysulfone (PSU), polycarbonate (PC), polyacrylonitrile (PAN), polyamide (PA), polytetrafluorethylene (PTFE), or combinations thereof and B) at least one hydrophilic polymer selected from the group consisting of polyvinylpyrrolidone (PVP), polyethyleneglycol (PEG), polyvinylalcohol (PVA), and a copolymer of polypropyleneoxide and polyethyleneoxide (PPO-PEO); or
iv) any combination of i), ii), and iii).

4. A device according to claim 1, wherein the hollow fiber membrane of the third hollow fiber membrane dialyzer allows passage of substances having a molecular weight of up to about 45 kD with a sieving coefficient measured in whole blood of between about 0.1 and about 1.0.

5. A device according to claim 1, wherein the third hollow fiber membrane dialyzer is selected adsorbent chosen from the group consisting of activated carbon, carbon nanotubes, hydrophobic silica, styrenic polymers, polydivinylbenzene polymers, styrene-divinylbenzene copolymers, and any combination thereof.

6. A device according to claim 1, wherein the third hollow fiber membrane dialyzer comprises i) a combination of at least one activated carbon, at least one copolymer of styrene and divinylbenzene without any functional groups, and at least one copolymer of styrene and divinylbenzene carrying trimethylbenzyl ammonium functional groups, or ii) a combination of at least one copolymer of styrene and divinylbenzene without any functional groups, and at least one copolymer of styrene and divinylbenzene carrying trimethylbenzyl ammonium functional groups.

7. A device according to claim 1, wherein the third hollow fiber membrane dialyzer comprises a fiber packing density in the range of from about 15% to about 50%.

8. A device according to claim 1, wherein the second hollow fiber membrane dialyzer is configured for removing water-soluble toxins from the dialysate solution received from the first hollow fiber membrane dialyzer.

9. A device according to claim 1, wherein the adsorbent of the third hollow fiber membrane dialyzer is configured for binding or adsorbing protein-bound toxins from the dialysate solution received from the second hollow fiber membrane dialyzer.

10. A device according to claim 1, wherein the adsorbent of the third hollow fiber membrane dialyzer is configured for binding or adsorbing hepatic toxins from the dialysate solution received from the second hollow fiber membrane dialyzer.

11. A device comprising
  (a) a first hollow fiber membrane dialyzer comprising a filtrate side,
    wherein the first hollow fiber membrane dialyzer comprises a high-flux membrane having a molecular weight cut-off in water, based on dextran sieving coefficients, of between about 25 kD and about 65 kD and a molecular weight retention onset in water, based on dextran sieving coefficients, of between about 5 kD and about 10 kD,
    wherein the first hollow fiber membrane dialyzer is configured for perfusion on the filtrate side of the first hollow fiber membrane dialyzer with a dialysate solution in a direction opposite to blood flow within the first hollow fiber membrane dialyzer, and
    wherein the dialysate solution comprises human serum albumin (HSA);
  (b) a second hollow fiber membrane dialyzer comprising a filtrate side and a lumen side,
    wherein the second hollow fiber membrane dialyzer comprises a hollow fiber membrane,
    wherein the second hollow fiber membrane dialyzer is configured for receiving the dialysate solution from the first hollow fiber membrane dialyzer,
    wherein the second hollow fiber membrane dialyzer is configured for passing the dialysate solution through the lumen side of the second hollow fiber membrane dialyzer, and
    wherein the second hollow fiber membrane dialyzer is configured for perfusion on the filtrate side of the second hollow fiber membrane dialyzer with a buffered aqueous solution in a direction opposite to the passing of the dialysate solution through the lumen side of the second hollow fiber membrane dialyzer; and
  (c) a third hollow fiber membrane dialyzer comprising a filtrate side, a lumen side, and a filtrate space,
    wherein the third hollow fiber membrane dialyzer comprises a hollow fiber membrane,
    wherein the filtrate side of the third hollow fiber membrane dialyzer is configured to be in fluid connection only with the lumen side of the third hollow fiber membrane dialyzer,
    wherein the lumen side of the third hollow fiber membrane dialyzer is configured for receiving the dialysate solution from the second hollow fiber membrane dialyzer, and
    wherein the filtrate space of the third hollow fiber membrane dialyzer comprises at least one adsorbent.

12. A device according to claim 11, wherein the hollow fiber membrane of the second hollow fiber membrane dialyzer comprises a low-flux membrane having a molecular weight cut-off in water, based on dextran sieving coefficients, of between about 10 kD and about 20 kD and a molecular weight retention onset in water, based on dextran sieving coefficients, of between about 2 kD and about 4 kD.

13. A device according to claim 11, wherein
  i) the high cut-off membrane of the first hollow fiber membrane dialyzer comprises A) at least one hydrophobic polymer selected from the group consisting of polyarylethersulfone (PAES), polypropylene (PP), polysulfone (PSU), polycarbonate (PC), polyacrylonitrile (PAN), polyamide (PA), polytetrafluorethylene (PTFE), or combinations thereof and B) at least one hydrophilic polymer selected from the group consisting of polyvinylpyrrolidone (PVP), polyethyleneglycol (PEG), polyvinylalcohol (PVA), and a copolymer of polypropyleneoxide and polyethyleneoxide (PPO-PEO); or
  ii) the hollow fiber membrane of the second hollow fiber membrane dialyzer comprises A) at least one hydrophobic polymer selected from the group consisting of polyarylethersulfone (PAES), polypropylene (PP), polysulfone (PSU), polycarbonate (PC), polyacrylonitrile (PAN), polyamide (PA), polytetrafluorethylene (PTFE), or combinations thereof and B) at least one hydrophilic polymer selected from the group consisting of polyvinylpyrrolidone (PVP), polyethyleneglycol (PEG), polyvinylalcohol (PVA), and a copolymer of polypropyleneoxide and polyethyleneoxide (PPO-PEO); or
  iii) the hollow fiber membrane of the third hollow fiber membrane dialyzer comprises A) at least one hydrophobic polymer selected from the group consisting of polyarylethersulfone (PAES), polypropylene (PP), polysulfone (PSU), polycarbonate (PC), polyacrylonitrile (PAN), polyamide (PA), polytetrafluorethylene (PTFE), or combinations thereof and B) at least one hydrophilic polymer selected from the group consisting of polyvinylpyrrolidone (PVP), polyethyleneglycol (PEG), polyvinylalcohol (PVA), and a copolymer of polypropyleneoxide and polyethyleneoxide (PPO-PEO); or
  iv) any combination of i), ii), and iii).

14. A device according to claim 11, wherein the hollow fiber membrane of the third hollow fiber membrane dialyzer allows passage of substances having a molecular weight of up to about 45 kD with a sieving coefficient measured in whole blood of between about 0.1 and about 1.0.

15. A device according to claim 11, wherein the adsorbent of the third hollow fiber membrane dialyzer is selected from the group consisting of activated carbon, carbon nanotubes, hydrophobic silica, styrenic polymers, polydivinylbenzene polymers, styrene-divinylbenzene copolymers, and any combination thereof.

16. A device according to claim 11, wherein the adsorbent of the third hollow fiber membrane dialyzer comprises i) a combination of at least one activated carbon, at least one copolymer of styrene and divinylbenzene without any functional groups, and at least one copolymer of styrene and divinylbenzene carrying trimethylbenzyl ammonium functional groups, or ii) a combination of at least one copolymer of styrene and divinylbenzene without any functional groups, and at least one copolymer of styrene and divinylbenzene carrying trimethylbenzyl ammonium functional groups.

17. A device according to claim 11, wherein the third hollow fiber membrane dialyzer comprises a fiber packing density in the range of from about 15% to about 50%.

18. A device according to claim 11, wherein the second hollow fiber membrane dialyzer is configured for removing water-soluble toxins from the dialysate solution received from the first hollow fiber membrane dialyzer.

19. A device according to claim 11, wherein the adsorbent of the third hollow fiber membrane dialyzer is configured for binding or adsorbing protein-bound toxins from the dialysate solution received from the second hollow fiber membrane dialyzer.

20. A device according to claim 11, wherein the adsorbent of the third hollow fiber membrane dialyzer is configured for binding or adsorbing hepatic toxins from the dialysate solution received from the second hollow fiber membrane dialyzer.

* * * * *